US00PP25948P3

(12) United States Plant Patent
Olesen

(10) Patent No.: US PP25,948 P3
(45) Date of Patent: Sep. 29, 2015

(54) MINIATURE ROSE PLANT NAMED 'POULPAH057'

(50) Latin Name: ***Rosa* hybrid**
Varietal Denomination: Poulpah057

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 167 days.

(21) Appl. No.: 13/986,914

(22) Filed: Jun. 14, 2013

(65) Prior Publication Data

US 2014/0373216 P1 Dec. 18, 2014

(51) Int. Cl.
*A01H 5/02* (2006.01)

(52) U.S. Cl.
USPC ..... Plt./121

(58) Field of Classification Search
USPC ..... Plt./101, 116, 121
See application file for complete search history.

(56) References Cited

PUBLICATIONS

UPOV-PLUTO Plant Variety Database, International Union for Protection of New Varieties of Plants, Jan. 19, 2015, obtained for cultiver 'Poulpah057' (1 page total).*
'HelpMeFind' website for roses, clematis and peonies. Cultivar 'Poulpah057'. Retrieved from the Internet http://www.helpmefind.com/rose/pl.php?n=88787 (1 page total).*
"Poulsen Roser A/S" catalog; Retrieved from the Internet http://www.poulsenroser.com (1 page total).*

* cited by examiner

*Primary Examiner* — Susan McCormick Ewoldt

(57) ABSTRACT

A new miniature rose plant that has abundant, pink flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpah057'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2004 and the resulting seeds were planted in a controlled environment in Fredensborg, Denmark. The new variety, named 'Poulpah057', originated as a single seedling from the stated cross.

The new variety may be distinguished from its male pollen parent and female seed parent primarily by flower coloration and growth habit. The female seed parent has deep pink flowers while the claimed plant has petals with a light pink undersurface. The male pollen parent is about 35 cm in height while the claimed plant is about 20 cm in height.

The objective of the hybridization of this rose variety for commercial culture was to create a new and distinct variety with unique qualities, such as:

1. Uniform and abundant pink flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah057' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah057' was selected by the inventor as a single plant from the progeny of the hybridization in 2004.

Asexual reproduction of 'Poulpah057' by cuttings was first done by Mogens N. Olesen in the nursery in Fredensborg, Denmark in 2005. This initial and other subsequent propagations conducted in controlled environments have demonstrated that the characteristics of 'Poulpah057' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah057'. Specifically illustrated in the drawing are flowers at various stages of development, flower in parts, leaves, and stems. Illustrated plants are 3 months of age.

DETAILED DESCRIPTION OF THE VARIETY

The following is a description of 'Poulpah057', as observed in its growth in glasshouses in Half Moon Bay, Calif. Observed plants are 3 months of age and were cultivated in 4 inch. Color references are made using The Royal Horticultural Society (London, England) Colour Chart, 2001, except where common terms of color are used.

For a comparison, several physical characteristics of the rose variety 'Poulhi008', U.S. Plant Pat. No. 15,722. are compared to 'Poulpah057' in Chart 1.

CHART 1

| | 'Poulpah057' | 'Poulhi008' |
|---|---|---|
| Petalage: | 60 petals total, 15 of which are petaloids | 40 to 45 petals |
| Flower Diameter: | 50 mm | 80 mm |
| General Tonality of Flower Color: | Blend of Red Group 55B and 55C | Red Group 55B |

Flower and Flower Bud

Blooming habit: Continuous.

Flower bud:

*Size*.—Upon opening, 20 mm in length from base of receptacle to end of bud. 18 mm in diameter.

*Bud form*.—Ovate.

*Bud color*.—As sepals unfold, petals are Red Group 49A with Yellow-Green Group 145D at the base.

*Sepals*.—Upper Surface: Color: Yellow-Green Group 138B and Yellow-Green Group 147A at the apex. Texture: Smooth, moderately pubescent. Lower Surface: Color: Yellow Green Group 146A. Anthocyanin at the apex of some of the sepal margins the color of Greyed-Purple Group 183A. Texture: Smooth. Shape: Apex: Cirrhose. Base: Flat at union with receptacle. Margins: Margins have moderate to strong foliaceous appendages on three of the five sepals. Size: 36 mm long by 8 mm wide.

*Receptacle*.—Surface Texture: Smooth. Shape: Funnel shaped. Size: 5 mm tall and 6 mm wide. Color: Yellow Green Group 145A.

*Pedicel*.—Surface: Smooth with strong pubescence. Length: 25 mm on average. Diameter: Generally 4 mm. Color: Yellow-Green Group 145A. Strength: Strong.

*Borne*.—Singly.

Flower bloom:

*Fragrance*.—Light floral scent.

*Duration*.—As a pot plant, flowers last up to 28 days.

*Size*.—Flower diameter is 50 mm when open. Flower depth is 31 mm.

*Form*.—General shape is a hybrid tea with a high pointed center.

*Shape of flower, side view*.—Upon opening, the upper portion is flat and convex. The lower portion is a flattened convex.

Petalage: Under normal conditions, flowers have 60 petals total, 15 of which are petaloids.

Color:

*General tonality*.—On open flower, a blend of Red Group 55B and 55C.

*Upon opening, petals*.—The undersurface of outer petals is Red Group 55D shaded with Red Group 49C and distinct intonations of Green-White Group 157A. The upper surface is Red Group 49A and 49B blended. The base of the upper surface is Green-White Group 157A. Innermost petals are Red Group 54D shaded lightly with with Red Group 49D on the upper surface. Undersurface of the inner petals is Red Group 54B shaded with Red Group 49C.

*After opening, petals*.—Outermost petals are Red-Purple Group 62C, on the upper surface with a basal petal spot Green-White Group 157A. Red-Purple Group 62B with light intonations of Red Group 49D and distinct coloration of Green-White Group 157B on the lower surface. Innermost petals are Red-Purple Group 62B with basal intonations of Green-White Group 157A on the upper surface. Red-Purple Group 62B with intonations of Red-Purple Group 62D on the lower surface.

Petals:

*Petal reflex*.—Moderate to strong, within 2 mm of the margin.

*Margin*.—Entire with slight point at the apex. Weak undulations.

*Shape*.—Generally broad and elliptic. Apex shape: Rounded. Base shape: Rounded.

*Size*.—35 mm (l) by 40 mm (w).

*Texture*.—Smooth.

*Thickness*.—Average.

Petaloids:

*Quantity*.—15 on average.

*Shape*.—Symmetric. The apex is rounded with a cleft at center, and the base is acute.

*Color*.—Red Group 38A with central bar the color of Yellow-Orange Group 18C.

*Size*.—10 mm (l) by 8 mm (w).

Reproductive organs:

*Pollen*.—None Observed.

*Anthers*.—Size: 2 mm long. Color: Yellow-Orange Group 16B. Quantity: 20 on average.

*Filaments*.—Color: Yellow Group 8D. Length: About 3 mm.

*Pistils*.—Length: About 3 mm long. Quantity: 15 on average.

*Stigmas*.—Inferior relative to the length of the filaments and the height of the anthers. Color: Greyed-Yellow Group 161D.

*Styles*.—Color: Green-White Group 157A.

*Seed formation*.—Not observed.

Plant

Plant growth: Upright. Plants are about 20 cm in height, and 15 cm wide.

Stems:

*Color*.—Juvenile growth: Yellow-Green Group 144B. Mature growth: Yellow-Green Group 144A.

*Length*.—Canes are 12 cm from the base of the plant to the flowering portion.

*Diameter*.—3 mm.

*Internodes*.—On mature canes, there is an average distance of 27 mm between nodes.

*Surface texture*.—Young and mature wood is smooth.

Prickles:

*Incidence*.—6 per 10 cm of stem.

*Size*.—Average length: 5 mm.

*Color*.—Juvenile and mature prickles are Greyed-Red Group 182B.

*Shape*.—Linear.

Plant foliage:

*Compound leaf size.*—100 mm (l) by 85 mm (w).

*Quantity.*—4 leaves per 10 cm of stem.

*Leaf bearing angle to stem.*—90 degrees.

*Color of juvenile foliage.*—Upper Leaf Surface: Yellow-Green Group 146A with anthocyanin Greyed-Purple Group 187A at margins. Lower Leaf Surface: Yellow-Green Group 146B.

*Color of mature foliage.*—Upper Leaf Surface: Yellow-Green Group 147A. Lower Leaf Surface: Yellow-Green Group 147B.

Plant leaves and leaflets:

*Stipules.*—Size: About 6 mm in length. Shape: Linear, slightly broad based with outward extending apecies. Margins: Finely serrated with few stipitate glands. Color: Yellow-Green Group 144A.

*Petiole.*—Length: 27 mm on average. Diameter: About 2 mm. Upper surface: Greyed-Purple Group 187B. Lower surface: Yellow-Green Group 144A.

*Rachis.*—Length: 28 mm on average. Diameter: About 2 mm. Upper surface: Greyed-Purple Group 187B. Lower surface: Yellow-Green Group 144A.

*Leaflet.*—Number of leaflets: 5 on normal leaves in middle of the stem. Size: 60 mm in length by 40 mm wide. Margin: Serrate. General Shape: Elliptical. Apex Shape: Acute. Base Shape: Cordate. Texture: Smooth. Arrangement: Odd pinnate. Venation: Reticulate. Leaf Gloss: Slightly glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpah057', substantially as illustrated and described herein, due to its abundant, pink flowers, vigorous growth, compact habit, suitability for production from softwood cuttings in pots, and durable flowers and foliage that make the variety suitable for distribution in the floral industry.

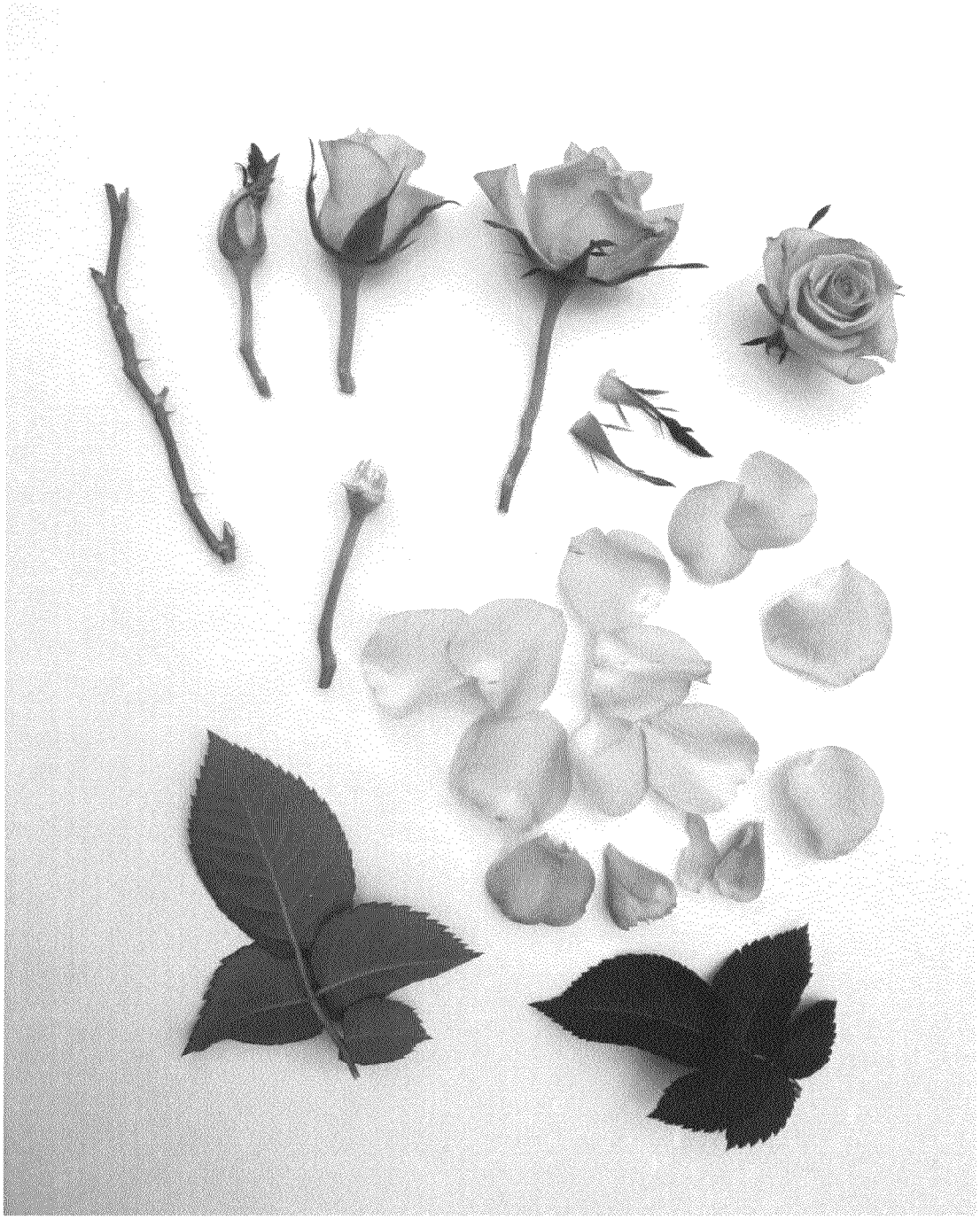

* * * * *